US008500768B2

(12) United States Patent
Cohen

(10) Patent No.: US 8,500,768 B2
(45) Date of Patent: Aug. 6, 2013

(54) APPARATUS FOR SAFE PERFORMANCE OF TRANSSEPTAL TECHNIQUE AND PLACEMENT AND POSITIONING OF AN ABLATION CATHETER

(75) Inventor: Todd J. Cohen, Port Washington, NY (US)

(73) Assignee: Cardiac Inventions Unlimited Inc., Port Washington, NY (US)

( * ) Notice: Subject to any disclaimer, the term of this patent is extended or adjusted under 35 U.S.C. 154(b) by 0 days.

(21) Appl. No.: 13/105,820

(22) Filed: May 11, 2011

(65) Prior Publication Data

US 2012/0065597 A1    Mar. 15, 2012

Related U.S. Application Data

(60) Provisional application No. 61/333,307, filed on May 11, 2010.

(51) Int. Cl.
*A61B 17/32* (2006.01)

(52) U.S. Cl.
USPC ........................................................ 606/167

(58) Field of Classification Search
USPC ................. 604/528, 533, 534, 535, 536, 538, 604/539; 606/1, 108, 139, 144, 145, 148, 606/167, 170, 184, 185, 213, 215; 623/1.11, 623/1.12
See application file for complete search history.

(56) References Cited

U.S. PATENT DOCUMENTS

| 5,211,638 | A | * | 5/1993 | Dudar et al. ................... 604/539 |
| 5,848,997 | A | * | 12/1998 | Erskine et al. ................ 604/533 |
| 6,071,274 | A | * | 6/2000 | Thompson et al. ........... 604/528 |
| 6,146,374 | A | * | 11/2000 | Erskine et al. ................ 604/533 |
| 6,676,694 | B1 | * | 1/2004 | Weiss ........................... 623/1.11 |
| 7,056,294 | B2 | * | 6/2006 | Khairkhahan et al. ......... 600/585 |
| 7,316,679 | B2 | * | 1/2008 | Bierman ....................... 604/535 |
| 7,618,072 | B2 | * | 11/2009 | Funamura et al. ............. 285/386 |
| 2003/0023138 | A1 | * | 1/2003 | Luscombe ....................... 600/30 |
| 2006/0009715 | A1 | * | 1/2006 | Khairkhahan et al. ......... 600/585 |
| 2006/0009737 | A1 | * | 1/2006 | Whiting et al. ................ 604/135 |
| 2011/0208215 | A1 | * | 8/2011 | Modesitt et al. ............... 606/151 |
| 2011/0276038 | A1 | * | 11/2011 | McIntyre et al. ................. 606/1 |

* cited by examiner

*Primary Examiner* — Ryan Severson
*Assistant Examiner* — Jonathan W Miles
(74) *Attorney, Agent, or Firm* — William H. Dippert; Eckert Seamans Cherin & Mellott, LLC

(57) ABSTRACT

A steerable catheter system to perform a transseptal puncture procedure comprises a steerable catheter shaft with at least one inner lumen, and an inner element slidably positioned within a shaft lumen, wherein the distal tip of the shaft can be deflected, counter-deflected, rotated, and counter-rotated and wherein the inner element can be deployed or retracted. In one embodiment, a single steerable catheter is capable of performing an intended procedure and a transseptal procedure all in one, wherein the catheter comprises an outer steerable catheter and an inner element which can be deployed to perform a transseptal puncture, and wherein, once the inner element crosses the inter-atrial septum, the catheter itself can slide forward without advancement of the inner element.

8 Claims, 10 Drawing Sheets

APPARATUS FOR SAFE PERFORMANCE OF TRANSSEPTAL TECHNIQUE AND PLACEMENT AND POSITIONING OF AN ABLATION CATHETER

CROSS-REFERENCE TO RELATED APPLICATION

This application is based upon and claims the benefit of the filing date of U.S. Provisional Patent Application Ser. No. 61/333,307, filed May 11, 2010, incorporated herein by reference in its entirety.

FIELD OF THE INVENTION

This application is directed to safe performance of transseptal technique. More particularly, this invention relates to the safe performance of transseptal technique and the placement and positioning of a left-side therapy and/or device such as an ablation catheter, left atrial appendage occlusive device, percutaneous valve or clip, or some other left-sided cardiac procedure, such as valvuloplasty.

BACKGROUND OF THE INVENTION

The performance of a transseptal procedure is an essential part of a number of left-sided procedures for left-side therapy and/or device such as an ablation catheter, left atrial appendage occlusive device, percutaneous valve or clip, or some other left-sided cardiac procedure, such as valvuloplasty although currently used most frequently for percutaneous catheter ablation of atrial fibrillation. To successfully ablate and isolate the pulmonary veins (and other structures within the left atrium), a transseptal needle is typically advanced from the femoral vein into the right atrium and across the inter-atrial septum to place a long sheath into the left atrium. Such a sheath is necessary to position an ablation catheter in the left atrium and access left atrium tissue, including the pulmonary veins.

Many of these transseptal and ablation procedures are performed under administration of therapeutic warfarin, which subjects the patient to additional bleeding risks from the transseptal and/or ablation procedures. Even if anatomical landmarks are used with fluoroscopic guidance (i.e., catheter visualization) and intracardiac echocardiography, there are significant risks. Cardiac perforation with resultant life threatening cardiac tamponade (the filling of fluid into the sac around the heart which impedes blood flow out of the heart) has been reported in one percent of these patients.

Patients with paroxysmal atrial fibrillation may have fairly normal cardiac substrates with normal sized left atriums. The pressure that results from tenting of the foramena of the inter-atrial septum and the recoil of the needle (and lack of control as it penetrates cardiac tissue) has lead to the research and development of safer approaches for the transseptal and catheter ablation procedures.

In one approach a small needle within a J wire is used with the hope of blunting needle access in the left atrium. Even with this approach it is still possible to puncture the aorta or some other inadvertent tissue.

One problem with the standard transseptal approach is the mere fact that the needle travels from the safer right side of the heart to the more precarious left side of the heart. Structures that are at risk include: (1) the aorta, its root, and structures; (2) the left atrial wall; and (3) a coronary artery or vein.

A number of newer procedures may be performed by cardiac interventionalists who are much more comfortable with the retrograde aortic approach to the left heart than a standard right-sided septal approach. These doctors will want to place left atrial occlusive devices (such as the WATCHMAN® left atrial appendage closure technology from Boston Scientic Corporation) and perform left-sided valve procedures percutaneously (clips/valve repairs or replacements). A simple and safe retrogradw approach would allow these doctors to utilize their left-sided skills and thereby minimize complications rather than learn and perform the more risky and right-sided transseptal approach.

OBJECTS OF THE INVENTION

It is an object of this invention to provide a safer transseptal technique.

It is also an object of this invention to provide a method and device for positioning and placement of an ablation catheter, or any other left atrial/left heart device placement, therapy, or procedure.

It is a further object of this invention to provide a system and method of simultaneously operating on both sides of the heart (right and left), with the potential to "mate" both sides to enhance the safety and performance of a transseptal procedure and improve on the stability of a catheter (or catheters) within the heart. The mating can use fluoroscopy, 3-D mapping, tracers, transducers, and/or magnetic guidance/coupling.

This and other objects of the invention will become more apparent in the discussion below.

SUMMARY OF THE INVENTION

According to the invention, the risk of inadvertent perforation or the aorta, the left atrium, and other structures, can be minimized. To accomplish this goal, a catheter according to the invention incorporates a retractable inner element into, for example, an ablation catheter itself. This catheter is similar to a standard radiofrequency ablation catheter. However, the catheter comprises an inner element which can be advanced and/or retracted to perform the transseptal procedure within a single system. Such a catheter vastly simplifies the procedure and permits a safe, controlled transseptal approach (perhaps without the need for a long introducer sheath). This system places the catheter in a more standard fashion (i.e., from the right side).

An ablation catheter useful according to the invention has distal electrodes and is positioned in the right atrium near the foramen ovule. Good atrial contract is confirmed via an atrial electrogram as well as fluoroscopic position. Intracardiac echocardiography and/or non-fluoroscopic 3-D mapping can also assure the location. Once the foramen ovule is tented, a lever in the middle of the catheter control handle is slid forward to advance a firm inner element of small diameter, which can puncture the septum in a controlled fashion. Once across the septum the catheter can be advanced without advancing the inner element (the inner element maintains its position within the catheter lumen). Finally, the inner element can be retracted, which facilitates safe manipulation of the catheter and placement of the procedural and/or therapy device directly into the left atrium. This catheter itself could be an ablation catheter with a self-contained controllable transseptal puncture mechanism.

In another embodiment of the invention, a left-side "protective" catheter is designed to guide, shield, and protect left-sided heart structures during a standard transseptal needle puncture (performed from the right side of the heart). In essence, the left-sided catheter can help with left atrial imaging and location and serve as a protective shield to guide and "catch" a needle, stylet, or wire as it is delivered across the inter-atrial septum. Placement of this "protective" catheter using the standard imaging techniques will not be in the aorta and could abut up against the inter-atrial septum from the left side and can press against the septum and/or sheath, catheter, and/or transseptal puncture system on the right side to assure a septal location.

The protective catheter can be steered manually or robotically (i.e., remote mechanical or magnetic navigation) from the femoral artery (or another artery) up the aorta via the retrograde aortic approach using fluoroscopic guidance or some other imaging means across the aortic valve, and into the left ventricle. The catheter would then be positioned across the mitral valve into the left atrium and steered towards the inter-atrial septum on the left side. A protective shield would be deployed from the distal tip of the protective catheter and the location used to guide and protect the delivery of the transseptal needle from the right atrium to the left atrium. Once the needle crosses the septum, it could safely hit the deployed shield. The guidewire/sheath could be safely placed, and left atrial and aortic perforation is thereby minimized. Alternatively, a protective catheter could be placed on the right side to protect the reverse transseptal procedure initiated from the left side as described below. Also, a protective catheter on one side could interact with a magnetically driven or robotically driven protective system on the other side of the heart.

In another embodiment of the invention, the transseptal approach could be performed via an entirely different approach, namely, from the left side. A catheter with a lumen or a retractable right atrial access system could be placed via standard steerable means including manual manipulation or remote mechanical or magnetic navigation (via the retrograde aortic approach) into the left atrium and positioned towards the inter-atrial septum. One embodiment of the catheter could generate a signal from a distal tip electrode to confirm the electrical position (although the electrode is not an absolute requirement). Fluoroscopy or an internal imaging system (such as intracardiac echocardi-ography) or non-fluoroscopic 3-D imaging could record the catheter's location. Once in position, and pointed towards the right atrium, an inner element from a transseptal access system can be deployed and safely enter the right atrium. This inner element could be a retractable needle/stylet, or a guidewire, needle, or a combination thereof, or some other access system which can generate a hole in the atrial system in order to place an introducer sheath to permit placement of a therapy device with easy maneuverability within the left atrium. Once this occurs and entry is confirmed, a long introducer sheath introduced into the right atrium can be engaged, the catheter/wire can slide into the sheath, and the sheath could be advanced into the left atrium. The left atrial to right atrial directionality of a transseptal procedure would require a new set of tools (herein described) and provide a potentially safer procedure (due to the force vector of septal perforaction pointing towards safer lower pressured structures).

A male/female left/right heart apparatus could be designed for protective and safe access in which the transseptal procedure is initiated on the left side. A needle or fine guide wire or stylet/steerable catheter system designed for steerability on the left side of the heart with at least the ability to steer and deflect a catheter across two cardiac valves via the retrograde aortic approach can be utilized. Such a catheter can consist of a distal electrode to confirm specific type of tissue contact and the degree of contact. An inner deployable element can be used to perform the transseptal puncture. Once performed the catheter can be advanced into the female (long sheath) on the right side of the heart and the needle inside the catheter retracted. The sheath than can slide forward over the catheter into the left atrium and the inner left-sided catheter could then be withdrawn.

The above system has the following unique elements: First, the transseptal approach is from the left to the right side of the heart (which is opposite of the standard approach). And second, the catheter designed for transseptal puncture has specific steerability that would allow precise deflection (counter-deflection) and rotation (and counterclockwise rotation). This catheter could also be designed for magnetic navigation with an inner lumen or inner or distal puncture mechanism to facilitate the transseptal puncture or access. The catheter could be advanced through a standard vascular introducer sheath. The central core of the catheter design will be hollow to either encompass a separate deployable/retractable transseptal system. This system could be contained within the design of said catheter, and its deployment and retraction could be precisely controlled with a lever, knob, switch or controller contained within the handle. The transseptal system could have a limited access cable/wire/needle in which the needle and not the catheter is advanced by a predetermined distance. An element within the cable/wire/needle could test for pressure/flow/$O_2$ saturation and confirm right atrium entry. In addition, the inner element/lumen could be a stylet and/or needle and could be switched out for a guide wire, or a combination thereof.

Ultrasound imaging is also possible from this inner guide. This inner element also has similar recording elements and properties for the systems described. Once across in the right atrium the catheter could be advanced into a long sheath or steerable sheath which would mate with the catheter. The sheath could then advance across the atrial septum into the left atrium, and the left atrial catheter could then be removed.

An essential element of this system is the need for right and left-sided apparatuses to "mate." It is even conceivable that the left-sided system could cross over to the right and secure a right-sided element and pull it across into the left atrium. Once across, the sheath can than be advanced across the septum over the apparatus which served as a guide. For example, two magnetically coupled right and left sided devices could be used to draw the male and female elements into close proximity to facilitate a transseptal procedure. A magnetic long sheath (with or without steerability) could be placed from the right side in the atrium and a catheter (possibly magnetically driven and navigated) for performing the transseptal could be placed on the left side of the heart. The magnetic fields created by the two devices (at least one being magnetic or the other ferro-magnetic, i.e., magnet to magnet or magnet to a metal attracted to a magnet) could pull the tips together at the inter-atrial septum. The transseptal procedure could then be performed, the two devices coupled, and the introducer slid over the catheter or a guide wire in order to provide an entry access point for an ablation catheter into the left atrium. Alternatively, mechanical mechanisms for the attachment and release of the right and left sided catheters may help with either the transseptal or ablation procedure.

A control handle located at the proximal end of an ablation catheter having an inner element will have a catheter lever which can be used to control the delivery of the inner element to perform a transseptal procedure. When the catheter lever is pulled backward, the inner element is retracted from the tip of the catheter. When the catheter lever is pushed forward, the inner element is deployed such that a transseptal procedure is performed. The lever could also work in the reverse direction.

A stiff inner element of small diameter could easily pierce the inter-atrial septum and facilitate catheter access across the septum.

In another embodiment of the invention, a steerable catheter system to perform a transseptal puncture procedure, comprises:
- a steerable catheter shaft having a proximal portion, a distal portion, and at least one inner lumen,
- optionally a control handle integral with the proximal portion, and
- an inner element slidably positioned within a shaft lumen, wherein the distal tip of the shaft can be deflected, counter-deflected, rotated, and counter-rotated and wherein the inner element can be deployed or retracted.

In another embodiment of a catheter system of the invention, deployment or retraction of the inner element is controlled via a knob, button, lever, or switch on the catheter handle.

In another embodiment of a catheter system of the invention, deployment or retraction of the inner element is controlled without a switch.

In another embodiment of a catheter system of the invention, the inner element which is designed to safely engage and traverse the inter-atrial septum.

In another embodiment of a catheter system of the invention, the inner element has sensors to determine the appropriate location of the tip of the inner element.

In another embodiment of a catheter system of the invention, the inner element employs feedback from said sensors to guide the positioning of the inner element and the delivery of the ablation catheter.

In another embodiment of a catheter system of the invention, the sensors are magnetic sensors to facilitate magnetic navigation of the distal portion of the catheter.

In another embodiment of a catheter system of the invention, the inner element is capable of recording and/or displaying essential information to assure appropriate placement.

In another embodiment of a catheter system of the invention, the inner element would be radio-opaque and trackable on fluoroscopy.

In another embodiment of a catheter system of the invention, the inner element is a needle comprising a tapered end, a guide wire, a stylet, or a modality capable of generating a hole such as an RF, laser, or other energy probe.

In another embodiment of a catheter system of the invention, the inner element is conical and/or cylindrical.

In another embodiment of a catheter system of the invention, the inner element contains electrodes for recording contact with heart tissue.

In another embodiment of the invention, a single steerable catheter is intended to perform an intended procedure and a transseptal procedure all in one, wherein the catheter comprises an outer steerable catheter optionally with a control handle and an inner element which can be deployed to perform a transseptal puncture, and wherein, once the inner element crosses the inner-atrial septum, the catheter itself can slide forward without advancement of the inner element.

In another embodiment of a catheter of the invention, control on the handle can deploy an inner element to cross the atrial septum and then allow advancement over the inner element via said catheter.

In another embodiment of the invention, a system safely performs transseptal puncture in which an apparatus is capable of being employed from the left-atrium across the atrial septum into the right atrium.

In another embodiment of a system of the invention, the system comprises:
- a steerable catheter with an inner deployable and retractable transseptal element, and
- a right-sided, larger inner diameter female mating guide catheter,
- wherein the two catheters are capable of being guided towards one another to identify the inter-atrial septum, the steerable left-sided catheter's transseptal member being deployed across the septum and within the right-sided guide catheter, the steerable catheter then being advanced, without advancing the inner element, into the guide catheter, and then the guide catheter is advanced across the septum into the left atrium.

In another embodiment of an apparatus of the invention, an apparatus comprises a steerable catheter specifically designed to deploy a barrier or shield to provide a target for a transseptal needle, guide wire, stylet, or other puncture element crossing from one side of the heart to the other and to protect cardiac tissue from damage.

In another embodiment of a catheter system of the invention, the system comprises a steerable catheter with a shaft and optional handle and an inner element which when deployed creates a target and protective shield larger than the tip of the catheter and which is intended to guide another device on the other side of the heart across the inter-atrial septum.

In another embodiment of a catheter system of the invention, the catheter contains one or more electrodes to electrically locate structures via an imaging modality.

In another embodiment of a catheter system of the invention, the image modality is electrically, fluoroscopically, non-fluoroscopically, intracardiac echocardiography, or a combination of two or more thereof.

In another embodiment of a catheter system of the invention, once the distal tip of the catheter is positioned adjacent the inter-atrial septum, the system is capable of deploying the inner element and of deploying a large protective shield and target is deployed.

In another embodiment of a catheter system of the invention, wherein as on one side of the heart a transseptal procedural system is delivered towards the target and shield, the intent is to mate the two and at the same time protect the inner element from going beyond the shield and puncturing the wall of the left atrium.

In another embodiment of a catheter system of the invention, the inner element is a transseptal needle, guide wire, or stylet or an energy-generating probe capable of creating a hole, such as an RF or laser probe.

In another embodiment of the invention, a cardiac transseptal system comprises:
- a first catheter for deploying a transseptal element and crossing the inter-atrial septum and having a distal end, and
- a second catheter for providing protection and covering the element and having a distal end,
- wherein each catheter has one or more coils at its distal end and the magnetic fields of the distal ends of the two catheters are configured to draw both catheters together at or near the inter-atrial septum.

In another embodiment of a transseptal system of the invention, one catheter is an ablation catheter and the other catheter is an introducer sheath.

In another embodiment of a transseptal system of the invention, the catheters are configured such that one catheter can slide into the other and the larger catheter can cross the septum and provide access through its inner lumen to the other side of the heart.

In another embodiment of the invention, a system to safely perform transseptal puncture comprises an apparatus capable of crossing from the left-atrium across the inter-atrial septum into the right atrium.

In another embodiment of invention, a method to safely perform transseptal puncture comprises crossing an apparatus from the left-atrium across the inter-atrial septum into the right atrium, or vice versa.

In another embodiment of a catheter system of the invention, the system comprises a pair of right and left heart catheters designed to mechanically mate, wherein the two catheters are configured to draw both catheters together at or near the inter-atrial septum, wherein a mechanical element from a catheter on one side of the heart can grab and pull a second element from the other side of the heart to enhance the performance of a specific function, and wherein once the task is performed the pulling catheter can release the second catheter and both catheters can perform independent tasks or be withdrawn from the heart and circulatory system.

In another embodiment of a system of the invention, the function is a transseptal procedure.

In another embodiment of a system of the invention, the function is an ablation procedure.

In another embodiment of a system of the invention, two units can be configured such that one unit can slide into the other and the larger unit can cross the septum and provide access through its inner lumen to the other side of the heart.

In another embodiment of a system of the invention, a steerable catheter with an inner deployable and retractable inner transseptal element is delivered via an arterial approach via the retrograde aortic approach (male component) and the tip is placed in the left atrium; wherein a right-sided, larger inner diameter female mating guide catheter is positioned from the venous approach and placed in the right atrium; wherein the two catheters are guided towards one another to identify the inter-atrial septum; wherein, once identified, the steerable left-sided catheter's transseptal member is deployed across the septum and within the right-sided guide catheter; wherein the steerable catheter is then advanced, without advancing the inner element, into the guide catheter and then the guide catheter is advanced across the septum into the left atrium; and wherein the left-sided catheter is then removed, and an ablation catheter is then placed into the right-sided guide catheter and delivered into the left atrium. Or vice versa.

In another embodiment of a system of the invention, securing the distal ends of two catheters together provides additional functionality selected from the group consisting of strength, maneuverability, and stability within the heart.

In another embodiment of the invention, a method for safely transversing an inter-atrial septum, comprises:
 advancing a distal end of a catheter having a lumen into the left atrium of a patient so that the distal end contacts the inter-atrial septum;
 advancing a distal end of a guide wire through the distal end of the catheter across the inter-atrial septum into the patient's right atrium;
 advancing the distal end of the guide wire distally to a point where a sheath having a distal end can be engaged;
 advancing the sheath over the guide wire so that the distal end of the sheath enters the left atrium.

In another embodiment of a method of the invention, magnetic navigation is used to position the distal end of the catheter in the left atrium.

In another embodiment of a method of the invention, the catheter is advanced across the inter-atrial septum and the sheath is advanced over the catheter.

In another embodiment of a method of the invention, the guide wire and/or catheter are withdrawn.

In another embodiment of a catheter system of the invention, the sheath is a long, right-sided transseptal sheath.

In another embodiment of a catheter system of the invention, a guide wire, needle, stylet, or RF (or other energy) modality punctures the inter-atrial septum.

In another embodiment of a catheter system of the invention, a method for safely transversing an inter-atrial septum, comprises:
 advancing a distal end of a first catheter having magnetic coils and having a lumen into the left atrium of a patient so that the distal end contacts the inter-atrial septum;
 advancing a distal end of second catheter having magnetic coils and a lumen into the right atrium of a patient so that the distal end of the catheter contacts the inter-atrial septum;
 advancing a guide wire through the distal end of the first catheter across the inter-atrial septum into the lumen of the second catheter;
 advancing the distal end of the guide wire distally to a point where a sheath or dilator having a distal end can be engaged; and
 advancing the sheath or dilator over the guide wire so that the distal end of the sheath or dilator enters the left atrium.

In another embodiment of a catheter system of the invention, magnetic navigation is used to position the distal ends of the catheters.

In another embodiment of a catheter system of the invention, the first catheter is advanced across the inter-atrial septum and the sheath or dilator is advanced over the catheter.

In another embodiment of a catheter system of the invention, the guide wire and/or first catheter are withdrawn.

In another embodiment of a catheter system of the invention, the sheath is a long, right-sided transseptal sheath.

In another embodiment of the invention, a steerable catheter system to perform a transseptal puncture, mapping, and ablation procedure, comprises:
 a steerable catheter shaft having a proximal portion, a distal portion, and at least one inner lumen,
 an optional control handle integral with the proximal portion, and
 an inner element slidably positioned within a shaft lumen, wherein the distal tip of the shaft can be deflected, counter-deflected, rotated, and counter-rotated and wherein the inner element can be deployed or retracted.

In another embodiment of a catheter system of the invention, deployment or retraction of the inner element is controlled via a knob, button, lever, or switch on the catheter handle.

In another embodiment of a catheter system of the invention, deployment or retraction of the inner element is controlled without a switch.

In another embodiment of a catheter system of the invention, the catheter contains at least one distal electrode.

In another embodiment of a catheter system of the invention, the catheter contains at least two recording electrodes.

In another embodiment of a catheter system of the invention, the distal electrode permits the passage of an inner element for the purpose of crossing the inter-atrial septum.

In another embodiment of a catheter system of the invention, at least one of the electrodes could be used to perform a catheter ablation procedure.

In another embodiment of a catheter system of the invention, the distal electrode is enlarged and/or irrigated to perform radiofrequency catheter ablation.

In another embodiment of a catheter system of the invention, an inner element which is designed to safely engage and traverse the inter-atrial septum.

In another embodiment of a catheter system of the invention, the distal electrode has a central lumen for passage of the inner element.

In another embodiment of a catheter system of the invention, the inner element is designed for easy and safe passage across the inter-atrial septum.

In another embodiment of a catheter system of the invention, the inner element has sensors to determine the appropriate location of the tip of the inner element.

In another embodiment of a catheter system of the invention, the inner element employs feedback from said sensors to guide the positioning of the inner element and the delivery of the ablation catheter.

In another embodiment of a catheter system of the invention, the inner element could record and help display essential information to assure appropriate placement.

In another embodiment of a catheter system of the invention, the inner element would be radio-opaque and trackable on fluoroscopy.

In another embodiment of a catheter system of the invention, the inner element is a needle consisting of a tapered end.

In another embodiment of a catheter system of the invention, the inner element is conical and/or cylindrical.

In another embodiment of a catheter system of the invention, the inner element contains electrodes for recording contact with heart tissue.

In another embodiment of the invention, a single steerable catheter is intended to perform catheter ablation and the transseptal procedure all in one, wherein the ablation catheter comprises an outer steerable catheter with a controllable handle and an inner element which can be deployed to perform a transseptal puncture, and wherein, once the inner element crosses the atrial septum, the catheter itself can slide forward without advancement of the inner element.

In another embodiment of a catheter system of the invention, control on the handle can deploy an inner element to cross the atrial septum and then allow advancement over the inner element via said catheter.

In another embodiment of a catheter system of the invention, a system to safely perform transseptal puncture comprises an apparatus is capable of being employed from the left-atrium across the atrial septum into the right atrium, or vice versa.

In another embodiment of a catheter system of the invention, the system comprises:
 a steerable catheter with an inner deployable and retractable transseptal element, and
 a right-sided, larger inner diameter female mating guide catheter.
 wherein the two catheters are capable of being are guided towards one another to identify the inter-atrial septum, the steerable left-sided catheter's transseptal member being deployed across the septum and within the right-sided guide catheter, the steerable catheter then being advanced, without advancing the inner element, into the guide catheter, and then the guide catheter is advanced across the septum into the left atrium.

In another embodiment of the invention, an apparatus comprises a steerable catheter specifically designed to deploy a barrier or shield to provide a target for a transseptal needle or element crossing from one side of the heart to the other and to protect cardiac tissue from damage.

In another embodiment of a catheter system of the invention, the system comprises a steerable catheter with a shaft and handle and an inner element which when deployed creates a target and protective shield larger than the tip of the catheter and which is intended to guide another device on the other side of the heart across the inter-atrial septum.

In another embodiment of a catheter system of the invention, the catheter contains one or more electrodes to electrically locate structures via a myriad of imaging means (electrically, fluoroscopically, nonfluoroscopically, 3-D mapping, and/or via intracardiac echocardiography).

In another embodiment of a catheter system of the invention, once the distal tip of the catheter is positioned adjacent the inter-atrial septum, is capable of deploying the inner element and of deploying a large protective shield and target is deployed.

In another embodiment of a catheter system of the invention, wherein as on one side of the heart a transseptal procedural system is delivered towards the target and shield, the intent is to mate the two and at the same time protect the inner element (including a transseptal needle/stylet) from going beyond the shield and puncturing the wall of the left atrium.

In another embodiment of a system of the invention, a cardiac transseptal system comprises:
 a catheter for deploying a transseptal element and crossing the inter-atrial septum, and
 a catheter for providing protection and covering the element,
wherein each catheter has one or more coils at its distal end and the magnetic fields of the two catheters are configured to draw both catheters together at or near the inter-atrial septum.

In another embodiment of a system of the invention, one catheter is an ablation catheter and the other catheter is an introducer sheath.

In another embodiment of a system of the invention, the catheters are configured such that one catheter can slide into the other and the larger catheter can cross the septum and provide access through its inner lumen to the other side of the heart.

In another embodiment of the invention, a system and method safely perform transseptal puncture in which an apparatus is designed and employed from the left-atrium across the atrial septum into the right atrium.

In another embodiment of a catheter system of the invention, a system comprises a pair of right and left heart catheters designed to mechanically mate, wherein the two catheters are configured to draw both catheters together at or near the inter-atrial septum, wherein a mechanical element from a catheter on one side of the heart can grab and pull a second element from the other side of the heart to enhance the performance of a specific function, and wherein once the task is performed the pulling catheter can release the second catheter and both catheters can perform independent tasks or be withdrawn from the heart and circulatory system.

In another embodiment of a catheter system of the invention, the function is a transseptal procedure.

In another embodiment of a catheter system of the invention, the function is an ablation procedure.

In another embodiment of a catheter system of the invention, two units can be configured such that one unit can slide into the other and the larger unit can cross the septum and provide access through its inner lumen to the other side of the heart.

In another embodiment of a catheter system of the invention, a steerable catheter with inner deployable and retractable inner transseptal element is delivered via an arterial approach via the retrograde aortic approach (male component) and the tip is placed in the left atrium; wherein a right-sided, larger inner diameter female mating guide catheter is positioned from the venous approach and placed in the right atrium; wherein the two catheters are guided towards one another to identify the inter-atrial septum; wherein, once identified, the steerable left-sided catheter's transseptal member is deployed across the septum and within the right-sided guide catheter; wherein the steerable catheter is then advanced (without advancing the inner element) into the guide catheter and then the guide catheter is advanced across the septum into the left atrium; and wherein the left-sided catheter is then removed, and an ablation catheter is then placed into the right-sided guide catheter and delivered into the left atrium.

In another embodiment of a catheter system of the invention, securing the distal ends of two catheters together provides additional functionality selected from the group consisting of strength, maneuverability, and stability within the heart.

DETAILED DESCRIPTION OF THE INVENTION

Figure 1:
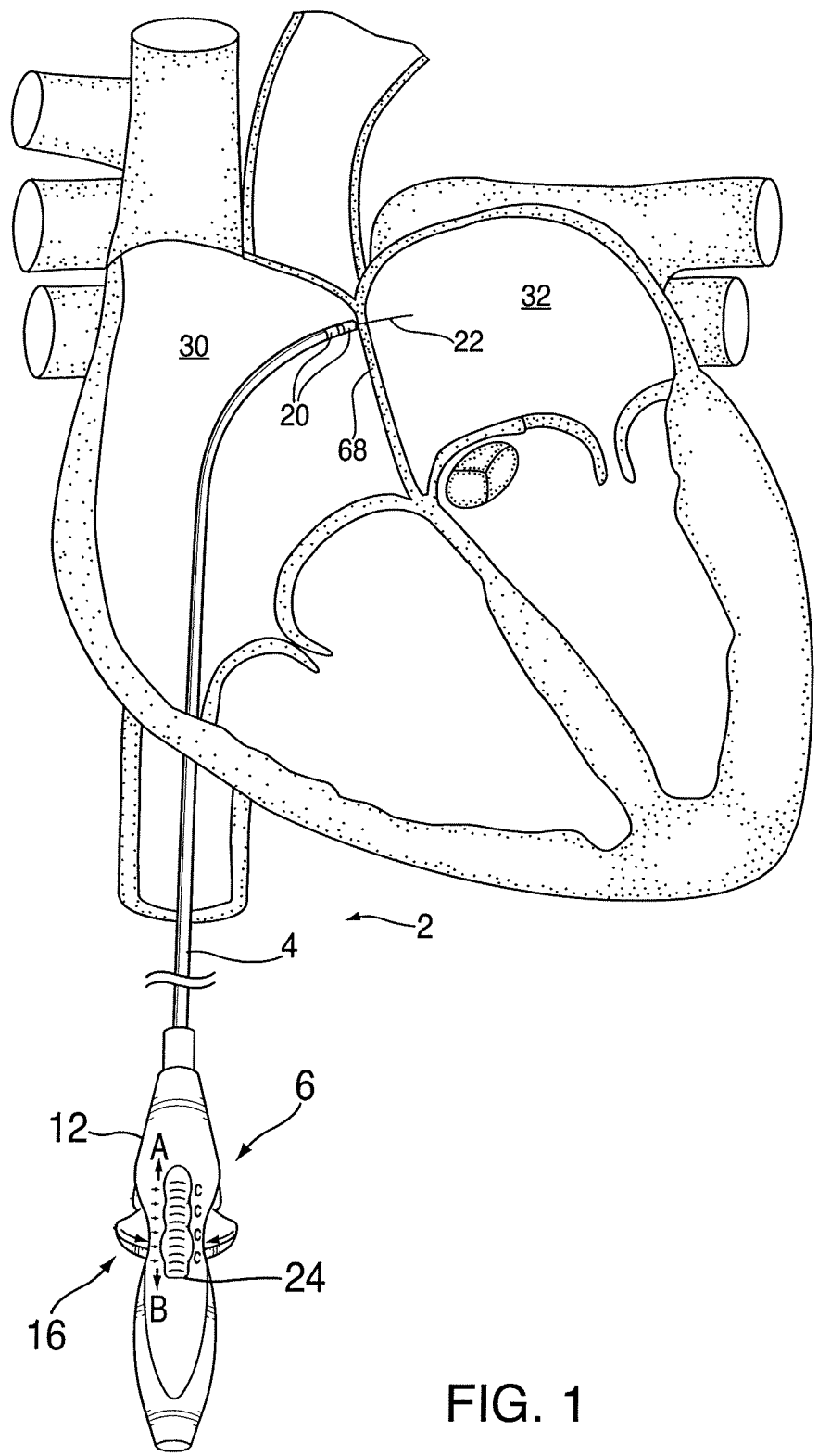
FIG. 1 is a schematic representation of an embodiment of a catheter system useful according to the invention.

The invention can perhaps be better appreciated by referring to the drawings. In FIG. 1, an ablation catheter 2 comprises a steerable catheter shaft 4, a proximal portion 6, and a distal portion 8. Proximal portion 6 comprises a control handle 12, to provide deflection, rotation, and articulation to distal portion 8. Control handle 12 has a deflection knob 14 and a counter-deflection knob 16. Distal portion 8 comprises at least two electrodes 20 and the distal portion of a retractable inner element 22. Inner element 22 is controlled by a lever 24 in or on control handle 12. When lever 24 is slid in the distal direction, inner element 22 advances, and when lever 24 is slid proximally, inner element 22 retracts. Preferably, when lever 24 is moved to the right, inner element is disengaged so that ablation catheter 2 can be advanced.

The distal portion 8 of catheter 2 is shown adjacent to or abutting the transseptal septum 28 between right atrium 30 and left atrium 32. Inner element 22 is shown to have perforated transseptal septum 28 at perforation 36.

Ablation catheter 2 can essentially be a standard radiofrequency ablation catheter. However, the catheter encompasses an inner element which can be deployed and retracted to perform a transseptal procedure within a single system. Catheter 2 is positioned in the right atrium near the foramen, and good atrial contract is confirmed via an atrial electrogram as well as fluoroscopic position. Intracardiac echocardiography can also assure the location. Once the distal portion 8 of ablation catheter 2 is advanced against septum 28 so that the foramen is tented, lever 24 is slid forward to advance inner element 22 to puncture septum 28 in a controlled fashion. Once septum 28 has been perforated, catheter 2 can be advanced without advancing inner element 22. Preferable inner element 22 is withdrawn distally to allow safe manipulation of ablation catheter 2.

Figure 2:
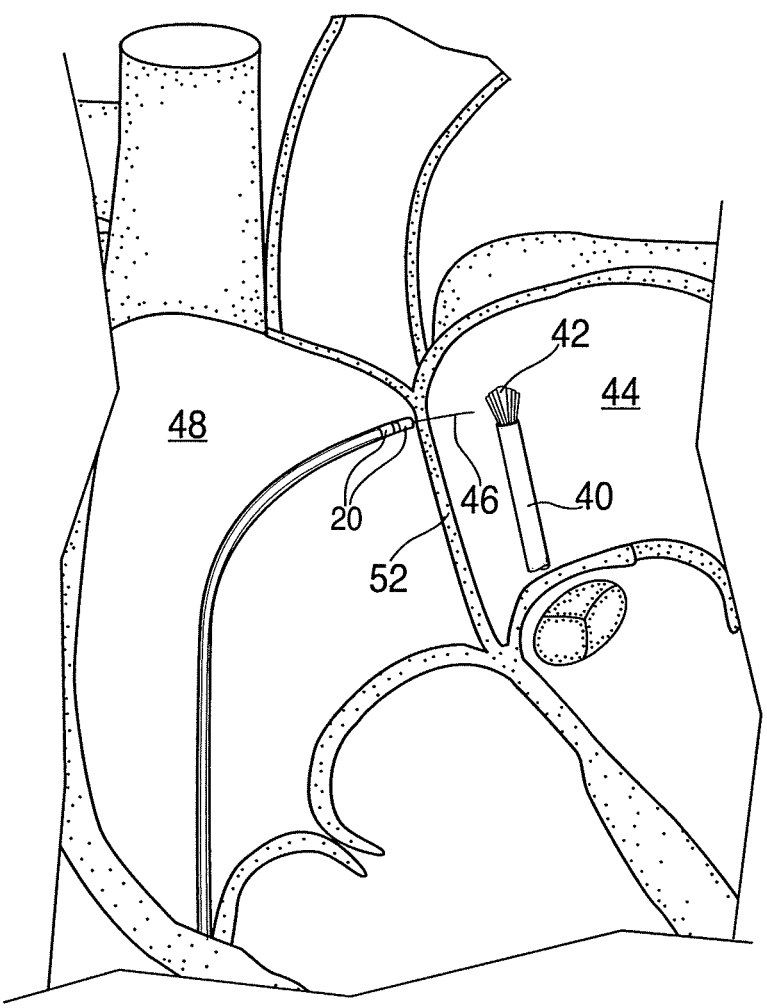
FIG. 2 is a schematic representation of a detail representing another embodiment of the invention.

In another embodiment of the invention, a left-side catheter guides, shields, and protects left-sided heart structures during a standard transseptal needle puncture (performed from the right side of the heart). FIG. 2 shows the design of such a system. In essence, a left-sided catheter 40 with a deployable protective shield 42 can help with imaging and location of left atrium 44 and serve as a protective shield to "catch" needle 46 as it is delivered from right atrium 48 across the inter-atrial septum 52. Needle 46 could be viewed as a ball thrown by a pitcher, and catheter/shield 40/42 could be viewed as a deployable catcher's mitt. Protective catheter 40 can be steered from the femoral artery (or another artery) up the aorta via the retrograde aortic approach using fluoroscopic guidance across the aortic valve, and into the left ventricle. Protective catheter 40 would then be positioned across the mitral valve into left atrium 44 and steered towards inter-atrial septum 52 on the left side.

The protective shield would be deployed and the location used to guide and protect the delivery of the transseptal needle 46 from the right to left atrium 44. Once needle 46 crosses septum 52, it could safely hit deployed shield 42. The guidewire/sheath could be safely placed and thereby minimize left atrial and aortic perforation.

Figures 3A, 3B, 3C:
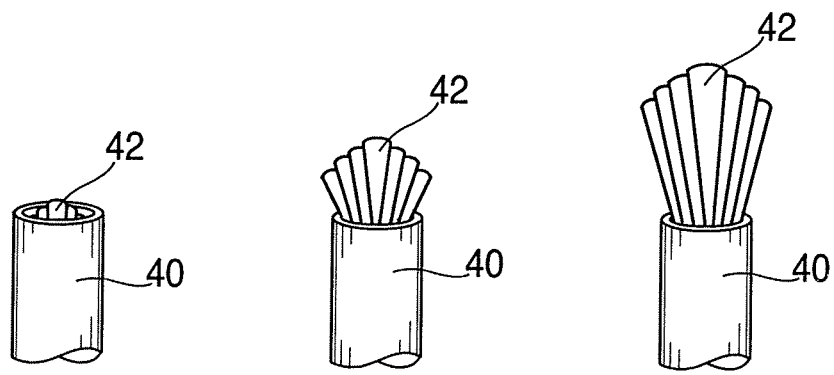
FIGS. 3A to 3C are schematic representations of the distal tip of a catheter useful according to the invention.

The distal tip 54 of catheter 40 is shown in three stages in FIGS. 3A to 3B, where protective shield 42 is not deployed at all (FIG. 3A), partially deployed (FIG. 3B), and then totally deployed (FIG. 3C). Protective shield 42 may comprise a flexible or rigid deployable material that can function to protect tissue from an inadvertent needle puncture. A nitinol or stainless steel mesh is an an example of useful material.

Figure 4:
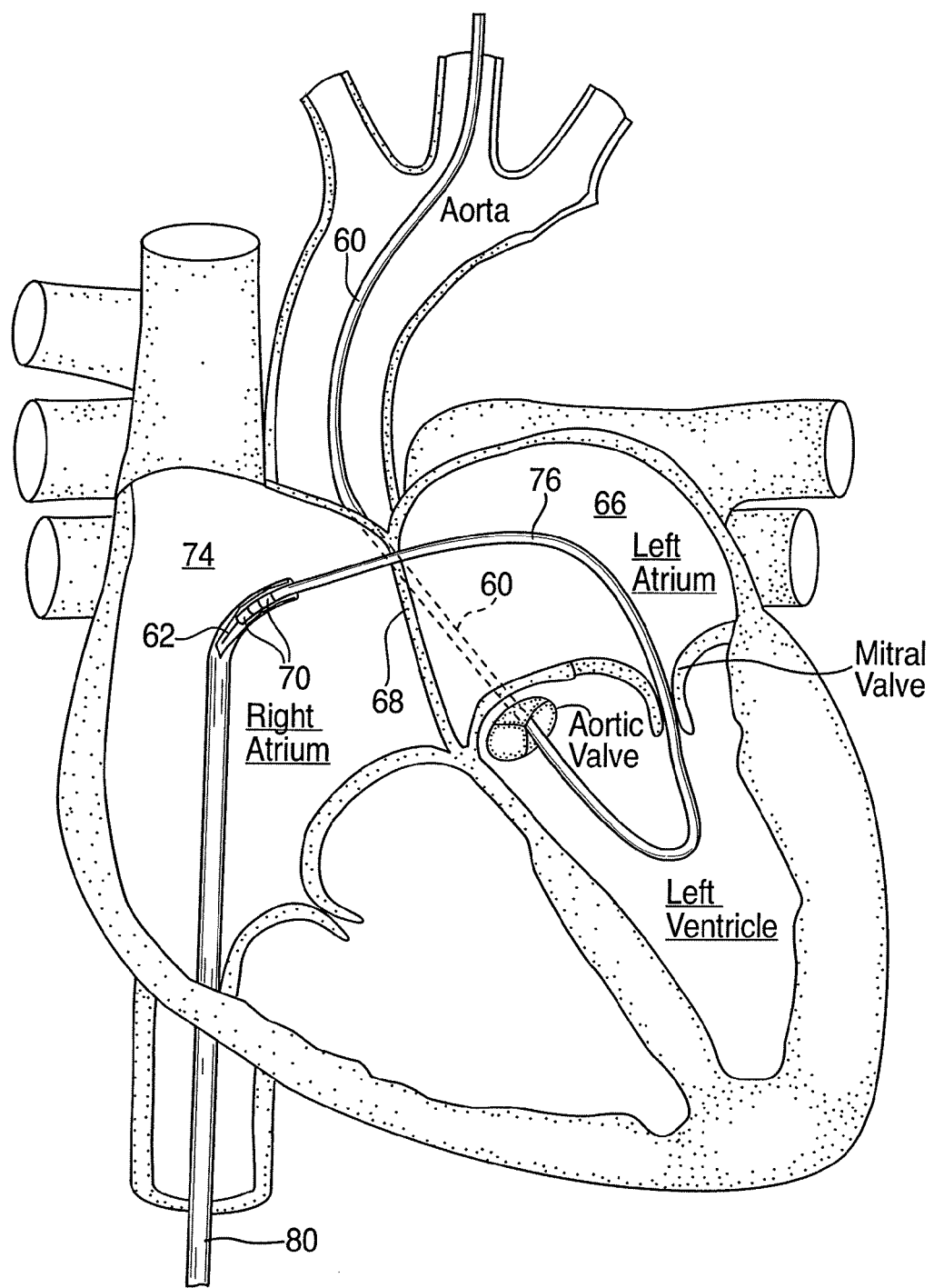
FIG. 4 is a schematic representation of a further embodiment of the invention.

An alternative, entirely different approach to performing a transseptal approach is shown in FIG. 4. A steerable ablation catheter 60 with a retractable inner element 62 lumen and a retractable right atrial access system could be placed via standard steerable means (via the retrograde aortic approach) through the aorta 64 into the left atrium 66 and positioned towards the inter-atrial septum 68. Catheter 60 could record from a tip electrode 70 and confirm the electrical position. Fluoroscopy or an internal imaging system (such as intracardiac echocardiography) could record the catheter's location. Once in position, and pointed towards right atrium 74, retractable needle 62 is deployed and the distal portion 76 of the transseptal access system can safely enter and potentially confirm entry to right atrium 74. Once this occurs, a long introducer sheath 80 can be engaged, and catheter/wire 60/42 can slide into sheath 80, and sheath 80 can be advanced into left atrium 66.

An essential aspect of certain embodiments of the invention is the need for right and left-sided apparatuses to "mate." It is even conceivable that the left sided system could cross over to the right atrium and secure a right-sided element and pull it across into the left atrium. Once across, the sheath can than be advanced across the septum over the apparatus which served as a guide.

Figure 5:
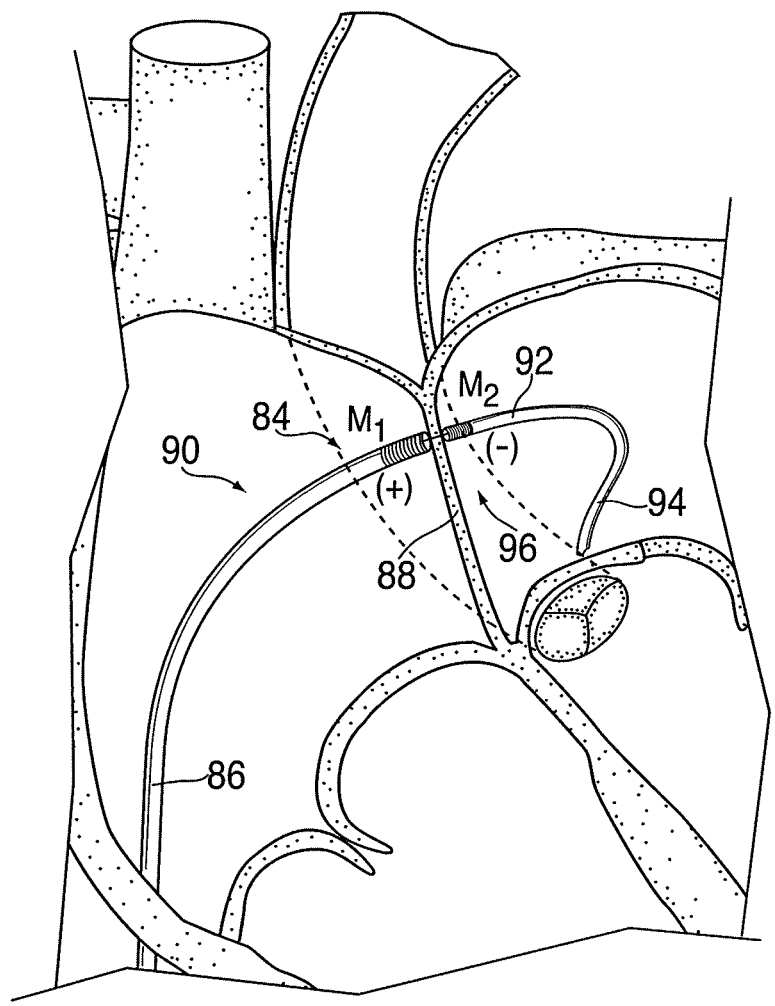
FIG. 5 is a schematic representation of yet another embodiment of the invention.

FIG. 5 shows two magnetically coupled right and left sided devices which could be used to draw the male and female elements in close proximity to facilitate a transseptal procedure. The distal tip 84 of a long sheath 86 (with or without steerability) is placed adjacent the inter-atrial septum 88 from the right atrium 90, and the distal tip 92 of a catheter 94 for performing the transseptal is positioned in the left atrium 96. Sheath distal tip 84 and catheter distal tip 92 each have magnetic coils, and the magnetic fields created by the magnetic coils can pull the respective distal tips 84 and 92 together at inter-atrial septum 88. The transseptal procedure could then be performed, sheath 86 and catheter 94 can be coupled, and introducer slid 86 can be slid over catheter 94 to provide an entry access point for an ablation catheter into left atrium 96.

Figure 6A:
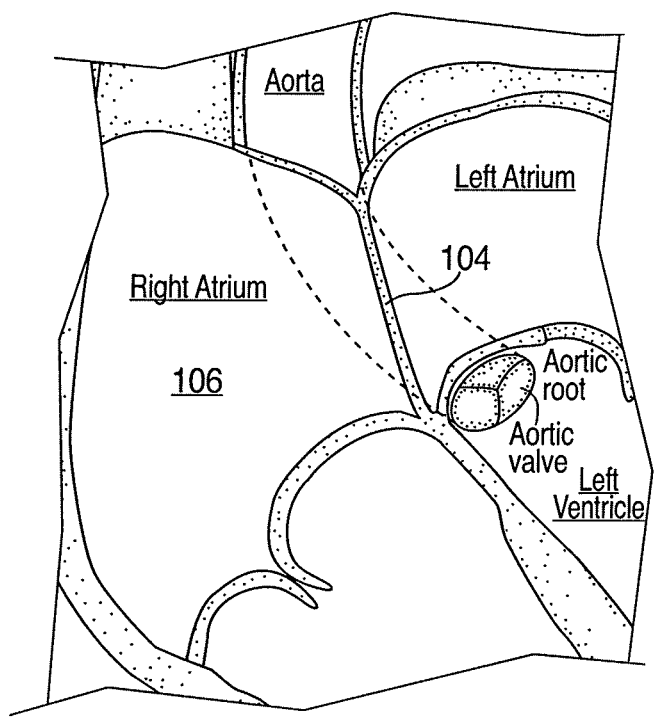
FIGS. 6A to 6E are schematic representations of a yet further embodiment of the invention.
Figure 6B:
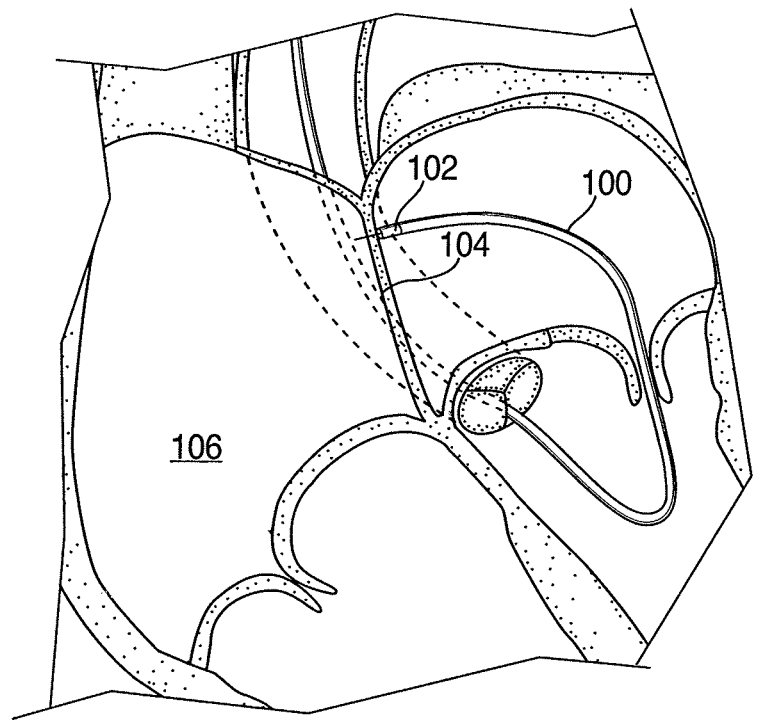
Figure 6C:
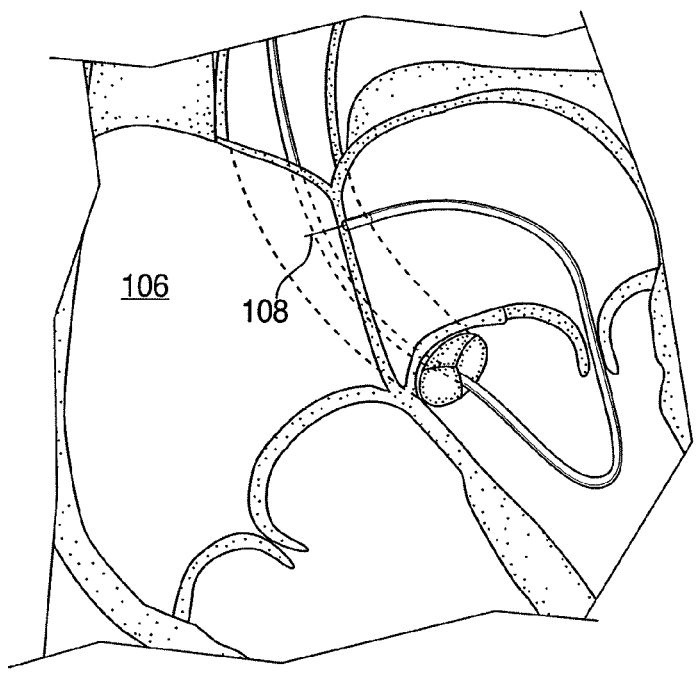
Figure 6D:
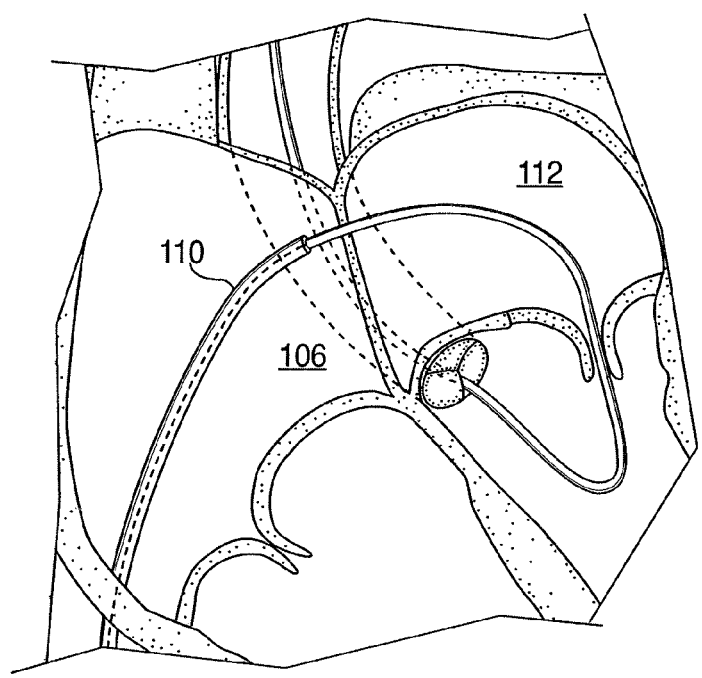
Figure 6E:
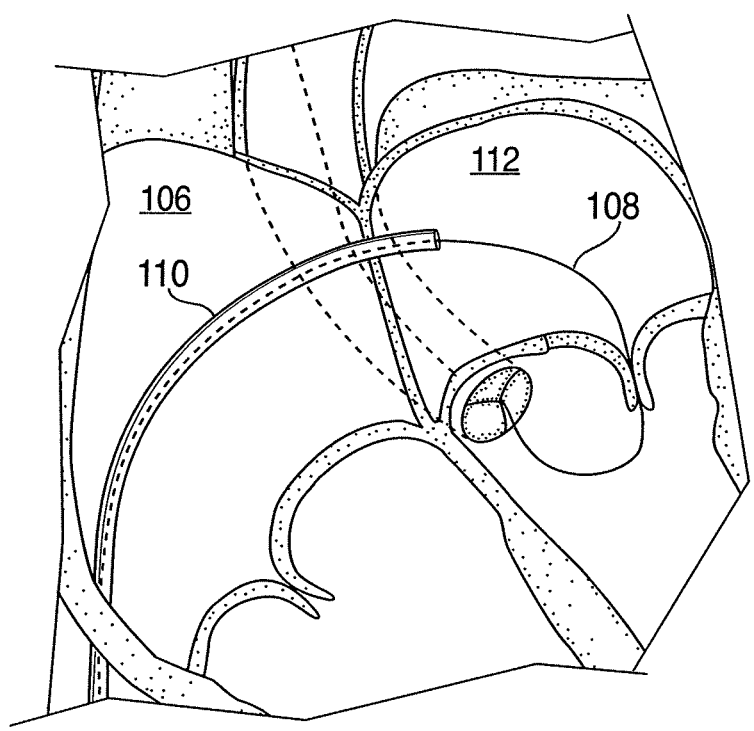

FIGS. 6A to 7D should be self-explanatory. FIGS. 6A to 6E show a safe transseptal puncture system using magnetic navigation. The heart's anatomy is shown in FIG. 6A, and FIG. 6B shows the magnetic navigation placing the distal tip 102 of a soft, flexible, magnetically driven catheter 100 using non-fluoroscopic 3D mapping at an inter-atrial septum 104 (technology available from Stereotaxis, St. Louis, Mo.) Tip 102 is positioned at inter-atrial septum 104 (preferably the foramen ovale) via retrograde aortic approach. A specifically designed inner punctive stylet, wire, needle, or combination thereof 108 is advanced in a controlled fashion into the right atrium 106 (FIG. 6C). In FIG. 6D, the distal portion of a long, right-sided transseptal sheath 110 has been advanced into right atrium 106, and wire 108 and/or catheter 100 are advanced across inter-atrial septum 104 to engage transseptal sheath 110, which could be coupled to and/or provide protection or a target for puncture. Sheath 110 is then advanced (with or without a dilator) over wire 108 and/or catheter 100 into left atrium 112, as shown in FIG. 6E. The distal portion of sheath 110 is in left atrium 112, and catheter 100 and/or wire 108 can be withdrawn. Sheath 110 is flushed and ready now for any left atrial procedure.

Figure 7A:
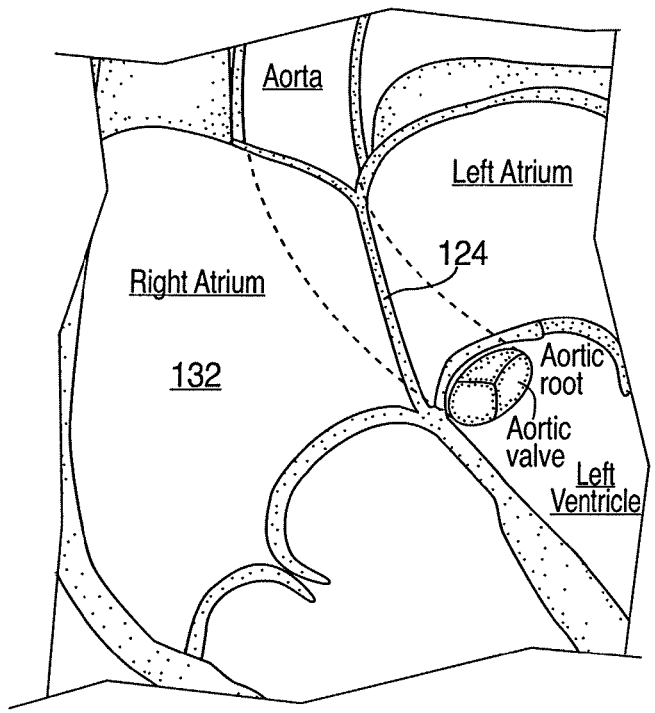
FIGS. 7 to 7D are schematic representations of a yet further embodiment of the invention.
Figure 7B:
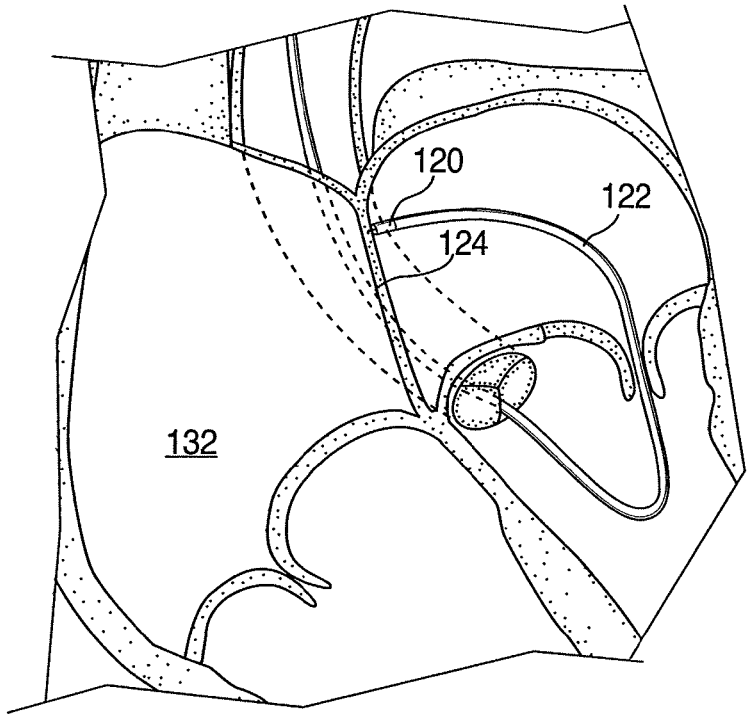
Figure 7C:
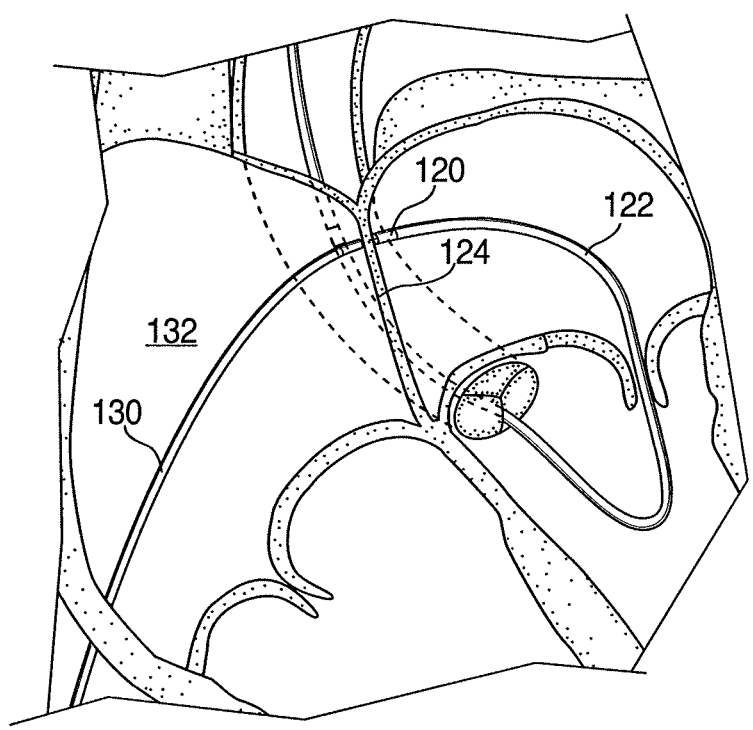
Figure 7D:
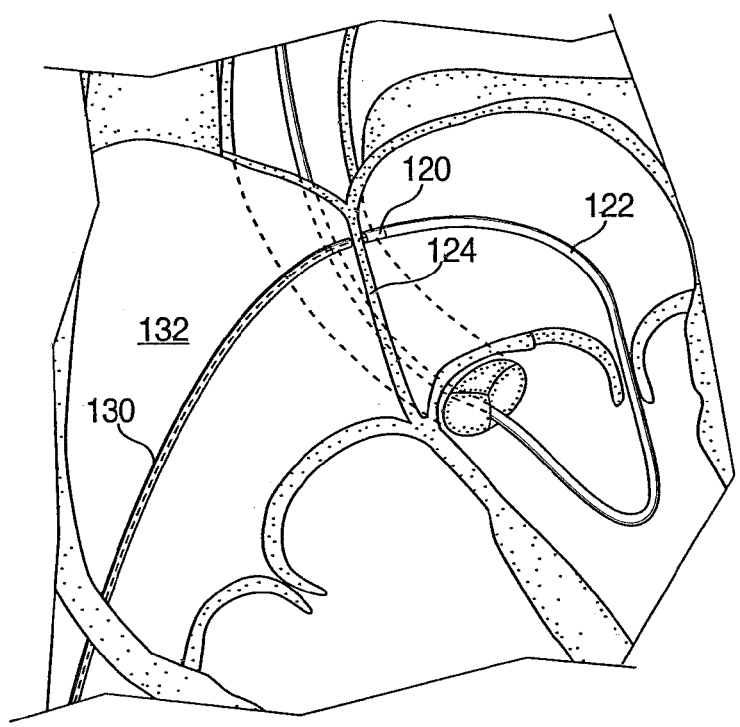

FIGS. 7A to 7D show an approach similar to that of FIGS. 6A to 6E using magnetic navigation and mating. The heart's anatomy is shown in FIG. 7A, and FIG. 7B shows magnetic navigation placing a distal tip 120 of a soft, flexible, magnetically driven catheter 122 using non-fluroscopic 3D mapping at an inter-atrial septum 124. Tip 120 is positioned at inter-atrial septum 124 (preferably the foramen ovale) from the femoral artery or some other arterial system via the retrograde aortic approach across the aortic valve and mitral valve. In FIG. 7C, distal tip 120 is held in place by a magnetic field, and the distal portion of a right-sided sheath or dilator/sheath system 130 is advanced into right atrium 132. Sheath 130 (introducer or even a catheter) with a marker, tracer, unipolar or bipolar electrode, transducer, magnetic coil or component or component with ferromagnetic properties 136 (which can be built-in to the tip of sheath 130 or turned on via coil activation) can mate (via either the magnetic field alone, fluoroscopy imaging, or 3D or other imaging) with distal tip 120. A guide wire, needle, or stiff angioplasty wire 128 can perform the transseptal procedure (going left to right) through a lumen of catheter 122. This could advance into right-sided sheath 130 on the right side of the heart which would slide over wire 128 and eventually across septum 124 (transseptal). This mating process can then allow guidance of a guide wire/needle/stylet/etc, through the left-sided catheter 122 into sheath 130. Wire 128 could be short or long; the simplest approach would be a very long wire which is now transseptal and extends the length of the right-sided sheath. A dilator could then slide over the wire and follow it up the right side into the right atrium and across inter-atrial septum 124. Sheath 130 could then follow, and the dilator/wire can be removed as well as the left-sided lumened catheter. The sheath would then be flushed and ready for an ablation catheter to be advanced into this long right-sided sheath into the left atrium for a left-sided procedure such as a valve repair, replacement, or atrial fibrillation ablation procedure.

An advantage of the training or exercising device described herein is that a user can easily exercise certain lower body muscles to include the core, legs, hips and/or thighs leg or thigh muscles as well as the cardio vascular system with a low impact, dynamic, relatively simple device.

While certain embodiments of the present invention have been illustrated and described, it will be clear that the present invention is not limited to these embodiments only. Numerous modifications, changes, variations, substitutions and equivalents will be apparent to those skilled in the art, without departing from the spirit and scope of the present invention, as described in the following claims.

The invention claimed is:

1. A system to safely perform transseptal puncture in which an apparatus is capable of being employed from the left-atrium across the atrial septum into the right atrium comprising: a steerable left-sided catheter with an inner deployable and retractable transseptal element, and a right-sided, larger inner diameter female mating guide catheter, wherein the two catheters are capable of being guided towards one another to identify the inter-atrial septum, the steerable left-sided catheter's transseptal member being deployed across the septum and within the right-sided guide catheter, the steerable left-sided catheter then being advanced, without advancing the inner element, into the guide catheter, and then the right-sided guide catheter being advanced across the septum into the left atrium.

2. A system to safely perform transseptal puncture in which an apparatus is capable of crossing from the left-atrium across the inter-atrial septum into the right atrium, or vice versa comprising: a steerable left-sided catheter with an inner deployable and retractable transseptal element, and a right-sided, larger inner diameter female mating guide catheter, wherein the two catheters are capable of being guided towards one another to identify the inter-atrial septum, the steerable left-sided catheter's transseptal member being deployed across the septum and within the right-sided guide catheter, the steerable left-sided catheter then being advanced, without advancing the inner element, into the guide catheter, and then the right-sided guide catheter being advanced across the septum into the left atrium.

3. A system comprising a pair of catheters designed to mechanically mate, wherein the two catheters are configured to draw both catheters together at or near the inter-atrial septum, wherein a first mechanical element from one of the catheters on one side of the heart can grab and pull a second element from the other catheter from the other side of the heart to enhance the performance of a specific function, and wherein once the task is performed the pulling catheter can release the other catheter and both catheters perform independent tasks or be withdrawn from the heart and circulatory system.

4. The system of claim 3 in which the function is a transseptal procedure.

5. The system of claim 3 in which the function is an ablation procedure.

6. The system of claim 3 in which the two catheters can be configured such that one catheter can slide into the other and the larger catheter can cross the septum and provide access through its inner lumen on the other side of the heart.

7. The system of claim 3, wherein one of the catheters is a steerable left-sided catheter with an inner deployable and retractable inner transseptal element, the steerable left-sided catheter is delivered via an arterial approach via the retrograde aortic approach and the tip is placed in the left atrium; wherein the other of the catheters is a right-sided, larger inner diameter female mating guide catheter, the guide catheter is positioned from the venous approach and placed in the right atrium; wherein the two catheters are guided towards one another to identify the inter-atrial septum; wherein, once identified, the steerable left-sided catheter's transseptal member is deployed across the septum and within the right-sided guide catheter; wherein the steerable left-sided catheter is then advanced, without advancing the inner element, into the guide catheter and then the guide catheter is advanced across the septum into the left atrium; and wherein the steerable left-sided catheter is them removed, and an ablation catheter is them placed into the right-sided guide catheter and delivered over a wire or without a wire into the left atrium.

8. The system of claim 3, wherein securing the distal ends of two catheters together provides additional functionality selected from the group consisting of strength, maneuverability, and stability within the heart.

* * * * *